US008855935B2

(12) United States Patent
Myres et al.

(10) Patent No.: US 8,855,935 B2
(45) Date of Patent: *Oct. 7, 2014

(54) METHOD AND SYSTEM FOR DISPLAYING GENETIC AND GENEALOGICAL DATA

(75) Inventors: Natalie M. Myres, Provo, UT (US); Scott R. Woodward, Alpine, UT (US); Luke A. D. Hutchison, Cambridge, MA (US)

(73) Assignee: Ancestry.com DNA, LLC, Provo, UT (US)

( * ) Notice: Subject to any disclaimer, the term of this patent is extended or adjusted under 35 U.S.C. 154(b) by 736 days.

This patent is subject to a terminal disclaimer.

(21) Appl. No.: 11/541,796

(22) Filed: Oct. 2, 2006

(65) Prior Publication Data

US 2008/0081331 A1  Apr. 3, 2008

(51) Int. Cl.
| | | |
|---|---|---|
| G01N 33/48 | (2006.01) | |
| G06F 19/26 | (2011.01) | |
| G06F 19/28 | (2011.01) | |

(52) U.S. Cl.
CPC ................ *G06F 19/26* (2013.01); *G06F 19/28* (2013.01)
USPC .......................................................... 702/19

(58) Field of Classification Search
None
See application file for complete search history.

(56) References Cited

U.S. PATENT DOCUMENTS

| | | | |
|---|---|---|---|
| 4,201,386 | A | 5/1980 | Seale et al. |
| 5,115,504 | A | 5/1992 | Belove et al. |
| 5,246,374 | A | 9/1993 | Boodram |
| 5,413,908 | A | 5/1995 | Jeffreys |
| 5,467,471 | A | 11/1995 | Bader |
| 5,978,811 | A | 11/1999 | Smiley |
| 6,049,803 | A | 4/2000 | Szalwinski |
| 6,105,147 | A | 8/2000 | Molloy |
| 6,277,567 | B1 | 8/2001 | Graziosi |
| 6,528,260 | B1 | 3/2003 | Blumenfeld et al. |
| 6,570,567 | B1 | 5/2003 | Eaton |
| 7,957,907 | B2 | 6/2011 | Sorenson et al. |
| 2003/0113727 | A1 | 6/2003 | Girn et al. |
| 2003/0172065 | A1 | 9/2003 | Sorenson |
| 2003/0204418 | A1 | 10/2003 | Ledley |
| 2004/0122705 | A1 | 6/2004 | Sabol et al. |
| 2004/0229231 | A1* | 11/2004 | Frudakis et al. ................ 435/6 |
| 2004/0243531 | A1 | 12/2004 | Dean |
| 2006/0020398 | A1 | 1/2006 | Vernon et al. |
| 2006/0136143 | A1 | 6/2006 | Avinash |
| 2006/0161535 | A1 | 7/2006 | Holbrook |
| 2007/0037182 | A1 | 2/2007 | Gaskin et al. |

OTHER PUBLICATIONS

International Search Report for International Application No. PCT/US07/20884 dated Mar. 10, 2008.
PCT International Preliminary Report on Patentability, PCT/US2007/020884, dated Apr. 16, 2009.
Wilson et al., "Geneological Inference from Microsatellite Data," Genetics (1998) 150:499-510.
Website printout, Family Tree DNA, http://www.familytreedna.com/main.html, Feb. 8, 2001 (2 pages).
Website printout, Oxford Ancestors, http://www.oxfordancestors.com, Feb. 12, 2001 (4 pages).
"Genealogy" definition, Merriam-Webster Online Dictionary, 2004, http://www.m-w.com/cgi-bin/dictionary?book=Dictionary&va=genealogy (1 page).
Corach et al., "Mass disasters: Rapid molecular screening of human remains by means of short tandem repeats typing," Electrophoresis (1995) vol. 16, pp. 1617-1623.
Butler, John M., "Commonly Used Short Tandem Repeat Markers," Forensic DNA Typing, Chapter 5, 2001, pp. 53-54, Academic Press.
Stedman's Medical Dictionary 27th Edition, 2000, p. 703.
United States Office Action, U.S. Appl. No. 11/864,218, Jul. 31, 2009, 14 pages.
United States Office Action, U.S. Appl. No. 11/864,218, Feb. 25, 2010, 12 pages.
United States Advisory Action, U.S. Appl. No. 11/864,218, Jun. 15, 2010, 3 pages.
United States Office Action, U.S. Appl. No. 11/864,218, Apr. 21, 2011, 14 pages.
United States Office Action, U.S. Appl. No. 11/864,218, Nov. 14, 2011, 17 pages.

* cited by examiner

*Primary Examiner* — Eric S Dejong
(74) *Attorney, Agent, or Firm* — Fenwick & West LLP

(57) ABSTRACT

A method and system for displaying genetic and genealogical data includes displaying indicators of related individuals. At least one genetically related individual is identified from a genetic database in response to a genetic input of an inquiring individual. Indicators of the inquiring individual and each of the at least one genetically related individual are displayed. The system includes a computer system having a display device, a processor device, a database and media having computer-executable instructions configured to display indicators of related individuals according to a method. The method includes identifying at least one genetically related individual from a genetic database in response to a genetic input of an inquiring individual and geographically displaying indicators of the inquiring individual and each of the at least one genetically related individual.

26 Claims, 15 Drawing Sheets

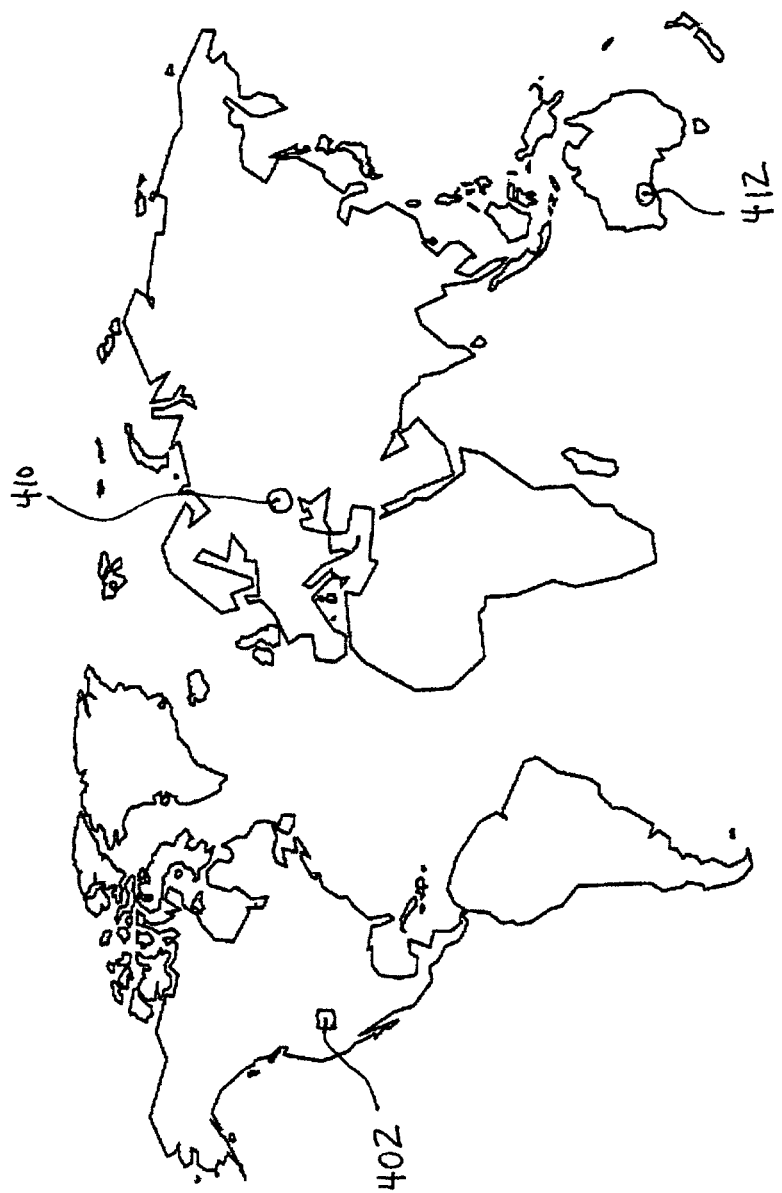

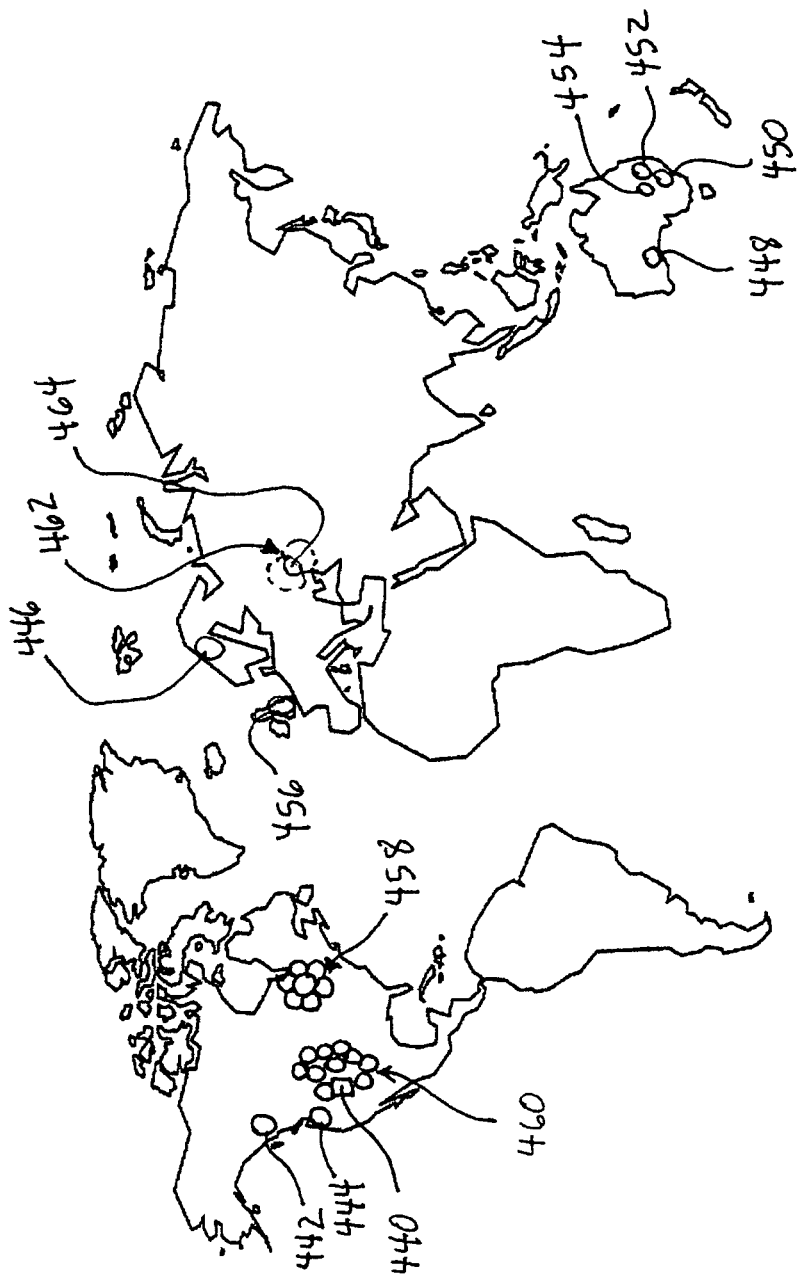

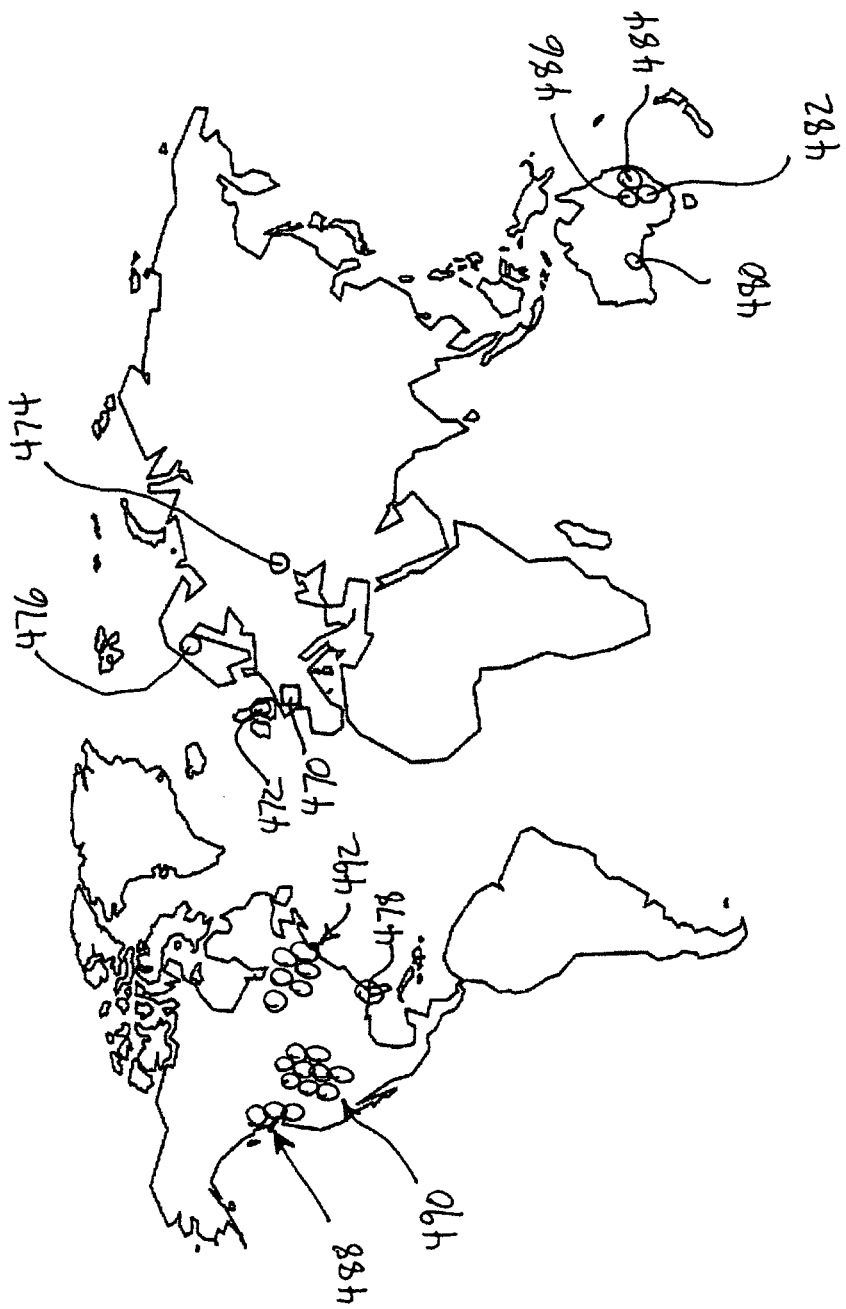

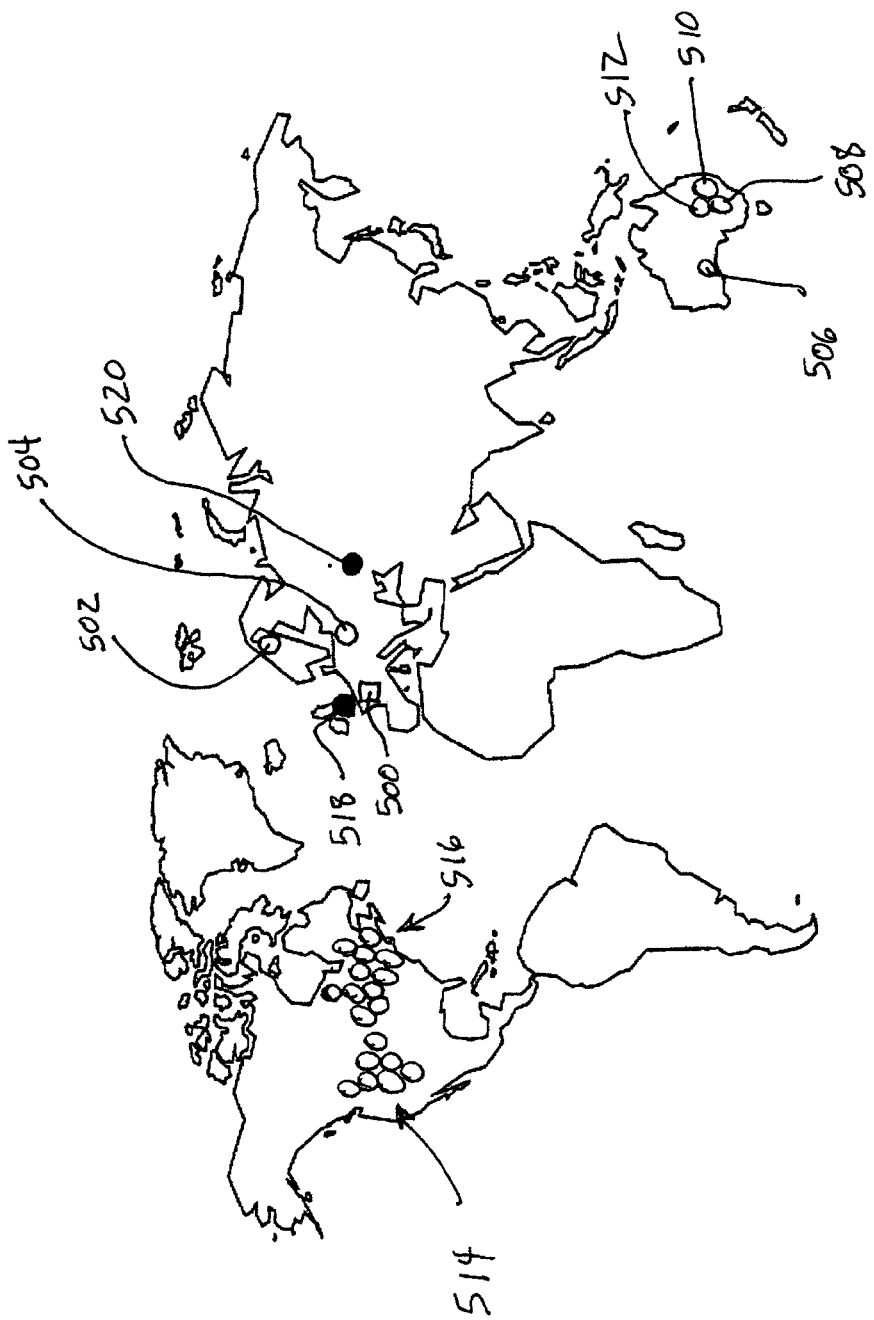

METHOD AND SYSTEM FOR DISPLAYING GENETIC AND GENEALOGICAL DATA

CROSS-REFERENCE TO RELATED APPLICATIONS

The present application is related to U.S. patent application Ser. No. 11/864,218 entitled METHOD AND SYSTEM FOR DISPLAYING GENETIC AND GENEALOGICAL DATA, filed Sep. 28, 2007, pending, which is a continuation-in-part of the present application and which is assigned to the Assignee of the present application. The present application is related to U.S. patent application Ser. No. 10/113,901 entitled METHOD FOR MOLECULAR GENEALOGICAL RESEARCH (as amended), filed Mar. 29, 2002, pending.

BACKGROUND OF THE INVENTION

1. Field of the Invention

The present invention pertains generally to the organization and presentation of data having familial relationship and, more particularly, to a system and method for displaying genetic and genealogical data.

2. State of the Art

Familial relationships or genealogy are traditionally defined according to a pedigree chart based solely upon record keeping. Genealogical record keeping has traditionally involved isolated efforts to assemble and maintain stores of information about progenitors for progeny and different cultures have created unique methods for maintaining genealogical records. Some tribes in western Africa, for example, have designated individuals who are reputed to recount by memory the names of scores of generations of ancestry and considerable additional detailed information about many individual ancestors. Most western civilizations have normally maintained written records to store such names and information, including records of births, christenings, marriages, deaths, military, civic and other governmental involvement. Much of this information is accessible on microfiche and on any of a variety of electronic media, including the Internet.

Unfortunately, the history of some people and communities has been lost or destroyed through time. In such instances, written documents are uninformative or simply do not exist. For example, descendants of slaves are often unable to locate any records of their ancestors. Illegitimacy or adoption may obstruct information or prevent access to records of biological ancestors. Similarly, immigration records may not accurately reflect the country of origin or complete surname of an individual. All of these circumstances can present significant obstacles for individuals trying to trace their "roots." Additionally, written information relies, by its nature, on the correctness of the source. Inaccuracies in such records are rife due to limited memory, human error and purposeful efforts to conceal inconvenient or embarrassing facts.

Identification of familial relationships may also be supplemented by genetic similarities or relationships. Such "molecular genealogy" merges the science of genetics with the study of genealogy and provides an alternative method of identifying genealogical information. By utilizing the genetic record that each individual retains of his/her past, it is possible to reveal important clues as to his/her origin and relationship to any other person or population.

Molecular genealogy links individuals together in "family trees" based on the unique identification of genetic markers. A genetic marker represents a specific location on a chromosome (locus) where the basic genetic units can exist as polymorphisms. For example, a difference of a single nucleotide with another at a particular location on a chromosome is called a Single Nucleotide Polymorphism (SNP), or point mutation. Various types of polymorphisms are used in genetic genealogy, examples of which include Single Nucleotide Polymorphism (SNP), Short Tandem Repeat (STR), etc. Variant copies at any chromosomal location are termed alleles. Different combinations of polymorphisms on a particular chromosome can be arranged as haplotypes. The more closely related two individuals are, the more alleles they will share in common. Any two individuals may share alleles at one or a few locations. However, examination of several dozen or hundreds of chromosomal locations will uncover differences even among closely related persons. The compilation of multiple genetic markers is referred to as a genotype and can serve as a unique genetic identifier for any given individual. To reconstruct molecular genealogies, it is necessary to utilize known biological relationships and correlate this information with the transmission of genetic markers through time.

Information encoded in the DNA of an individual and/or population can be used to determine the relatedness of individuals, families, tribal groups, and populations. Pedigrees based on genetic markers can reveal relationships not detectable in genealogies based only on names, written records, or oral traditions. The fact that DNA is inherited from both biological parents means that DNA can be used not only to create unique identifiers, but also to identify members of the same family, the same clan or tribal group, or the same population.

Prior art genetic record keeping systems and methods, fueled significantly by the human genome project, identify genetic characteristics of individual members of human and other species. Some records are directed to genetic characteristics in common between and among two or more individual members of a given biological sample, irrespective of familial relation. Examples of such genetic characteristics include genes determinative of human eye, hair and skin color, height and other physical characteristics. Inter-species analyses and records have been pursued as well, such as the study of commonalities in the genetic make up of various primates. Similar genetic characteristics may be identified among intra-familial relations as a portion of a broader lineal genetic inheritance, such as a proclivity toward cancers, heart disease, obesity and other conditions in some family lines.

The study of any of a variety of genetic characteristics and their presence among a defined familial group has heretofore focused on medical applications within relatively few generations. Similarly, the nexus of the genealogical and genotypical disciplines finds expression only in a very limited sense in such fields as forensic science and paternity determinations, and then only for a relatively limited number of generations.

Some potential genealogical applications of genetic science are limited in their usefulness, such as the notion that all sons inherit their entire Y-chromosome from their fathers and all children inherit identical mitochondria from their mothers. Similarly, men of Jewish descent can determine whether they are of Cohanim lineage by examination of Y-chromosome genetic markers. Such sex-chromosome investigations are limited because they involve a limited number of genetic markers and are restricted to a particular lineage and a particular sex. As females do not have a Y-chromosome and males do not pass on their mitochondrial DNA, determining whether members of the opposite sex are related can be a complicated, multi-step process.

Methods exist for combining genetic science and genealogical information to enable identification of biological ancestral relations across multiple earlier generations to a degree that is more accurate than that afforded by mere memory or written records. Thus, a combination of genotypical and genealogical disciplines identify chromosomal fragments that are identical by descent to elucidate family ties between siblings, parents and children, and ancestors and progeny across many generations.

While disciplines for combining genetic information with genealogical information are developing, an insightful approach for displaying such data does not presently exist. Conventionally, genealogical data has been confined to depiction using a two dimensional "family tree" structure for depicting relationships. Therefore, a need exists for an intuitive approach for displaying information that is a combination of genealogical and genetic data.

BRIEF SUMMARY OF THE INVENTION

A method and system for displaying genetic and genealogical data is disclosed. In one embodiment of the present invention, a method of displaying indicators of related individuals is disclosed. At least one genetically related individual is identified from a genetic database in response to a genetic input of an inquiring individual. Indicators of the inquiring individual and each of the at least one genetically related individuals are graphically or geographically or otherwise displayed.

In another embodiment of the present invention, a computer system having a display device, a processor device, a database and media having computer-executable instructions configured to display indicators of related individuals according to a method is provided. The method includes identifying at least one genetically related individual from a genetic database in response to a genetic input of an inquiring individual and displaying indicators of the inquiring individual and each of the at least one genetically related individual.

BRIEF DESCRIPTION OF THE SEVERAL VIEWS OF THE DRAWINGS

In the drawings, which illustrate what is currently considered to be the best mode for carrying out the invention:

FIGS. 3A-3G illustrate graphical representations of the displayed information throughout the various steps of execution of the method illustrated in the flowchart of FIG. 2, in accordance with an embodiment of the present invention; and FIGS. 4A-4C illustrate graphical representations of the displayed information including incrementally coalescing indicators based upon haplotypes and the respective geographical mapping of haplotypes, in accordance with an embodiment of the present invention.

DETAILED DESCRIPTION OF THE INVENTION

The fundamental principle of genetic transmission, that all persons receive genetic material from their biological parents, allows one to determine the origin of genes based on common ancestry and known modes of inheritance. Because this process is repeated every generation, all individuals carry within their DNA a record of who they are and how they are related to all of the other people on the earth. As individuals trace their biological relationships into the past, lineages will begin to "coalesce" into common ancestors.

In order to determine the degree of relatedness between individuals, it is necessary to identify those genes, or marker values, that are identical due to shared ancestry. Different regions of DNA have the ability to identify individuals, link them to immediate family groups, extended family or clan affiliations, and larger populations. For example, specific regions of a DNA strand have properties that can identify an individual's identity (e.g., spacer), extended family or tribe (e.g., regulatory) and species (e.g., structural). The "structural" region of DNA is under strong selection pressure. As such, very few variations are found among individual members of the same species. By way of contrast, the "spacer" region of DNA is under almost no selection pressure. Therefore, an individual, or a family, can be identified by a unique "spacer" sequence. The "regulatory" region of DNA is under moderate to strong selection pressure; less selection pressure than the "structural" region but more than the "spacer" region.

Figure 1:
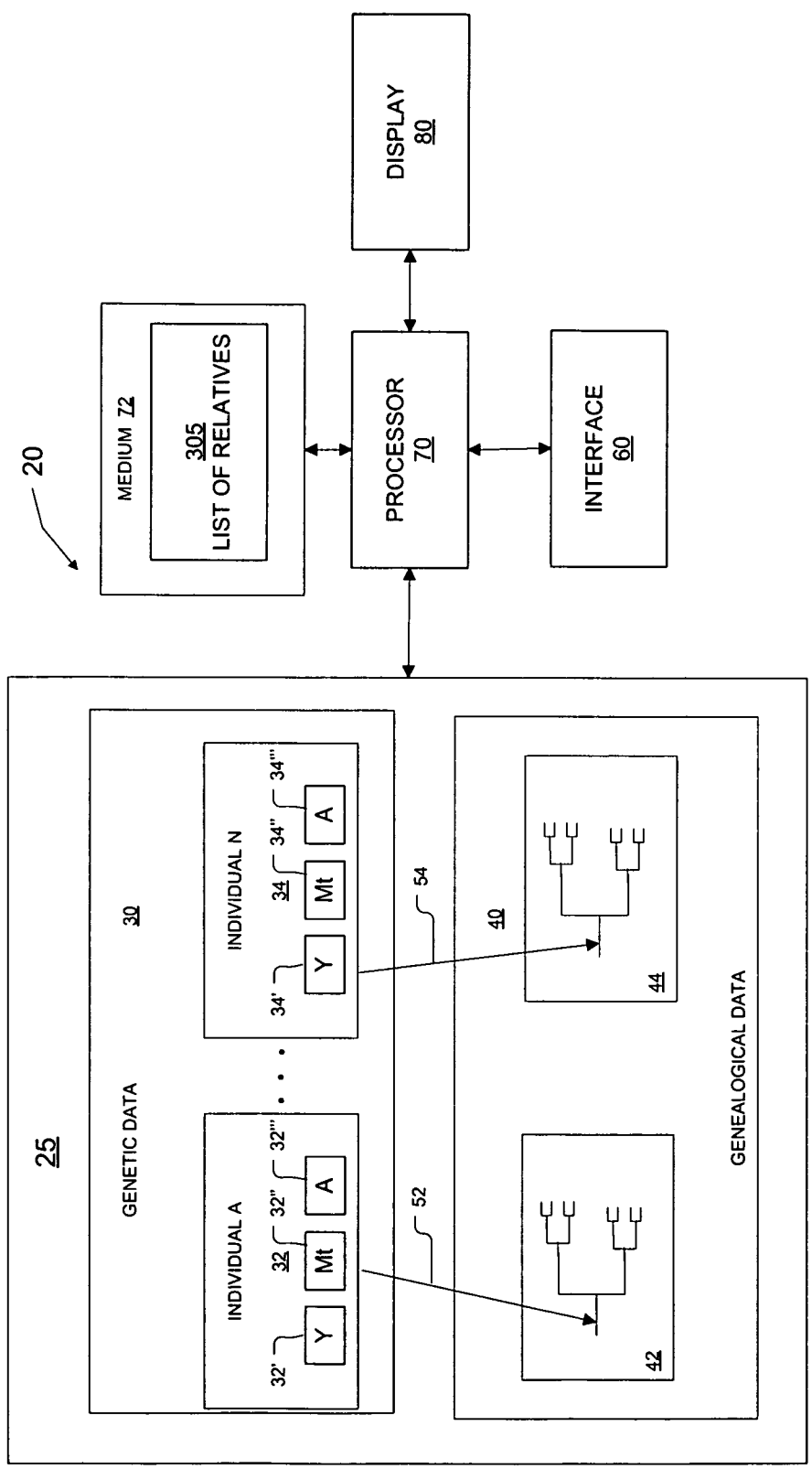
FIG. 1 illustrates a system for displaying familial relationships determined from genetic and genealogical data, in accordance with an embodiment of the present invention.

FIG. 1 illustrates a system for displaying familial relationships determined from genetic and genealogical data, in accordance with an embodiment of the present invention. A system 20 for displaying familial relationships includes a database 25 having data stored therein and is comprised of both genetic data 30 and genealogical data 40. Database 25 may be configured to store genetic data sets including genetic data 30 for a plurality of members and corresponding genealogical data sets including genealogical data 40 each extending any number of successively lineal ancestral familial generations. Genetic data 30 includes genetic data sets 32, 34 from a respective quantity of individuals A, N. Each of the genetic data sets 32, 34 includes data identifying at least one genetic marker or chromosomal fragment for each individual. A various quantity of genetic markers may be utilized depending on the extent of the chromosomal mapping and identification. Furthermore, the genetic data sets 32, 34 may include one or more combinations of Y-chromosome data (Y) or mitochondrial data (Mt) and the various genetic markers may be autosomal.

The genealogical records, when known, preferably include the given name and surname of each ancestor as well as each ancestor's date and place of birth. By examining each ancestor's place of birth, an individual can determine his or her national origin or ethnicity. When place of birth is not available, a place of christening, baptism, marriage or death can also be used to infer nationality and/or ethnicity. As geographically displaying of the location of an individual is described herein, the availability of geographical location data of an individual may be prioritized to include priority of known locations beginning with place of birth. The genealogical records may include or prioritize any additional information that might be of genealogical or genetic interest, for example, medical history, physical characteristics or personal accomplishments of each ancestor.

Relationships 52, 54, illustrated as pointers, cross-reference and associate the genetic data 30 and the genealogical data 40. For example, genealogical data 40 can be stored in a hierarchical format similar to a "family tree" wherein each individual or placeholder within the family tree has some recorded relationship with the other members of the hierarchical structure. For each individual data set 32, 34 in the genetic data 30, a corresponding genealogical data 42, 44 is present which correlates through relationships 52, 54 to the respective genealogical data 40.

The database 25 can be a part of a system 20 that also includes an inquiring individual interface 60. Interface 60 can be used for inputting the genetic data 30 and the genealogical data 40 into the database 25 and for creating the relationships 52, 54. A processor 70 and display 80 also cooperatively interact with interface 60 and database 25 to input data, identify relationships between the data and display the data as described hereinafter. The processor 70 provides a computational means for executing processes and methods for carrying out the receiving, processing and displaying of the data as described herein. Processor 70 is further configured to identify and describe a genetic pattern for a given data set, for example, a family tree. A genetic pattern might include a genetic marker, or chromosomal fragment, that is identical by descent. Processor 70 is further configured to correlate the genetic pattern for various family trees and predict an antecedent genetic pattern in the first family tree, for example, based on a statistical probability of relatedness. The various functions of processor 70 are executed according to methods stored in a medium 72. Medium 72 may be any form of an informational storage device including, but not limited to, magnetic, electronic, optical or otherwise.

Figure 2A:
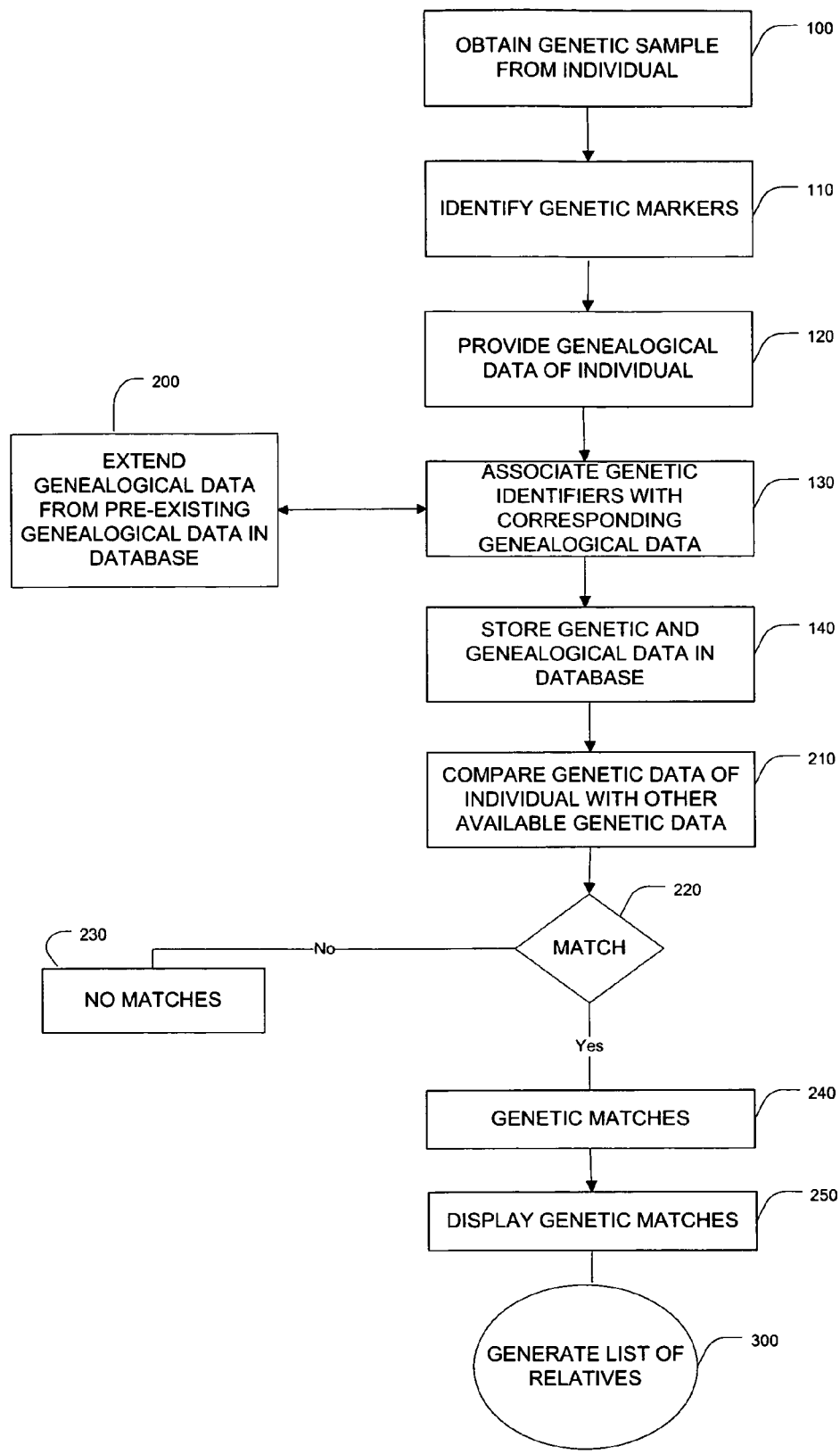
FIGS. 2A-2D illustrate a flowchart for displaying indicators of related individuals, in accordance with an embodiment of the present invention.

FIGS. 2A-2D illustrate a flowchart for displaying indicators of related individuals, in accordance with an embodiment of the present invention. FIGS. 3A-3G illustrate graphical representations of the displayed information throughout the various steps of execution of the method illustrated in the flowchart of FIG. 2. In FIG. 2A, a genetic sample is obtained 100 from an individual to be visibly displayed in relationship to other entries in the database that are genetically and genealogically related. Genetic information can be gathered by obtaining a small blood, saliva or hair sample from an individual. DNA is extracted from the sample in a laboratory and specific regions of DNA are amplified using, for example, a polymerase chain reaction ("PCR") and the PCR products are analyzed and the genetic markers are identified 110.

Several methods exist for identifying the genes or markers that are identical due to shared ancestry. Commonly employed genetic systems used to test relatedness are the Y-chromosome (Y-cs), mitochondrial DNA (mtDNA) and autosomal genes (A) or markers contained on the non-sex chromosomes. The Y-chromosome genetic data of individual A data set 32 and individual N data set 34 of FIG. 1 are respectively illustrated as genetic data 32' and 34'. Similarly, the mitochondrial DNA genetic data of individual A data set 32 and individual N data set 34 of FIG. 1 are respectively illustrated as genetic data 32" and 34". Additionally, the autosomal genetic data of individual A data set 32 and individual N data set 34 of FIG. 1 are respectively illustrated as genetic data 32''' and 34'''. While chromosomes exist in pairs in the nucleus of most cells, mtDNA is more numerous and is located outside the nucleus in the mitochondria.

Chromosomes are subject to recombination or shuffling every generation and are not necessarily inherited intact from generation to generation. This characteristic property of genetics contributes to the diversity found among peoples and is one of the mechanisms responsible for the unique genetic identity that defines an individual. Y-cs and mtDNA are novel in that they experience limited or no recombination. Y-cs DNA is inherited from father to son and mtDNA is inherited by all children from their biological mother but only passed on through daughters. Each of these systems can be differentially used to answer various questions of genealogical interest. Preferably, at least one of the genetic markers is autosomal thereby increasing the ease in which genealogical relationships can be inferred between two individuals of the opposite sex and ancestors can be inferred who are not in the direct paternal and/or maternal line.

Generally, many genetic markers may be examined for each genetic sample. The genetic markers may appear in sets in what is known as "linkage disequilibrium." Linkage disequilibrium is a condition where two genes are found together in a population at a greater frequency than that predicted simply by the product of their individual gene frequencies. Thus, the presence of a gene at a particular location on a chromosome creates a bias at another location. Analysis of sets of markers in linkage disequilibrium allows the determination of unambiguous haplotypes from the genotypic information at a physical location on a chromosome.

When an individual provides either the genetic sample and genetic marker values are identified, or the individual directly provides the genetic marker values from a previous determination, the individual further provides 120 genealogical data 40 (FIG. 1) corresponding to their known progenitors. Unique indexing identifiers are associated 130 to provide links or pointers between the genetic data and the genealogical data. By way of example and not limitation, the genetic data set 32 of individual A is associated with the genealogical data 42 through relationship 52 and the genetic data set 34 of individual N is associated with the genealogical data 44 through relationship 54 as illustrated with respect to FIG. 1. By way of example and not limitation, association 130 of the unique indexing genetic identifier may associate various genetic segments, an example of which may include a first segment which reflects a population, family and clan identifier (e.g., an "AFET" identifying all individuals of the same population), a second segment which reflects a familial relationship (e.g., MFF822), and a third segment which reflects an individual genotype or haplotype.

The individual's genetic data 30 and genealogical data 40 are stored 140 in the database 25 in association with the individual's unique indexing identifier. By way of example and not limitation, the genealogical data 40 includes the given name and surname, date of birth and place of birth of at least three, preferably four, generations of successively lineal ancestors. Genealogical data 40 can also include information regarding the family medical history or any other known information regarding an ancestor. The genealogical data 40 can be stored in a family tree format wherein the tree and each placeholder on the tree are designated by a genetic identifier. Deceased ancestors are assigned a genetic identifier based on a probability statement of the likelihood of the ancestor having a specific genotype or haplotype inferred from descendants. The genetic identifier may be interpreted in accordance with varying data stored in a persistent database layer and interpreted by various algorithmic processes and logic. Hence, analytical programming can retrieve and associate the genetic data 30 and genealogical data 40 corresponding to a particular genetic identifier or for a plurality of members of a population(s). The genealogical data provided by the individual may also be extended 200 by comparison with preexisting genealogical data 40 (FIG. 1) in the database 25 (FIG. 1). The comparison could consist, for example, of searching for similar given names and surnames. Analysis of strictly genealogical information may allow the inference of a biological relationship.

At this state of the process, the database has been populated with genetic data and with genealogical data. The various embodiments of the present invention provide methods and systems for geographically displaying the individuals and their "relatives" that have been identified through genetic similarities and genealogical data. In order to determine "relatives" identified by way of genetic similarities, a comparison 210 of the individual's genetic data set 32, for example, with the genetic data set 34 of the database 25 which could lead to the identification of biological relationships. A determination 220 of genetic matches may yield no matches 230 when the genetic data 30 is insufficiently populated with individuals or may yield one or more genetic matches 240 when genetically similar individuals have been included in the genetic data 30.

Figure 2B:
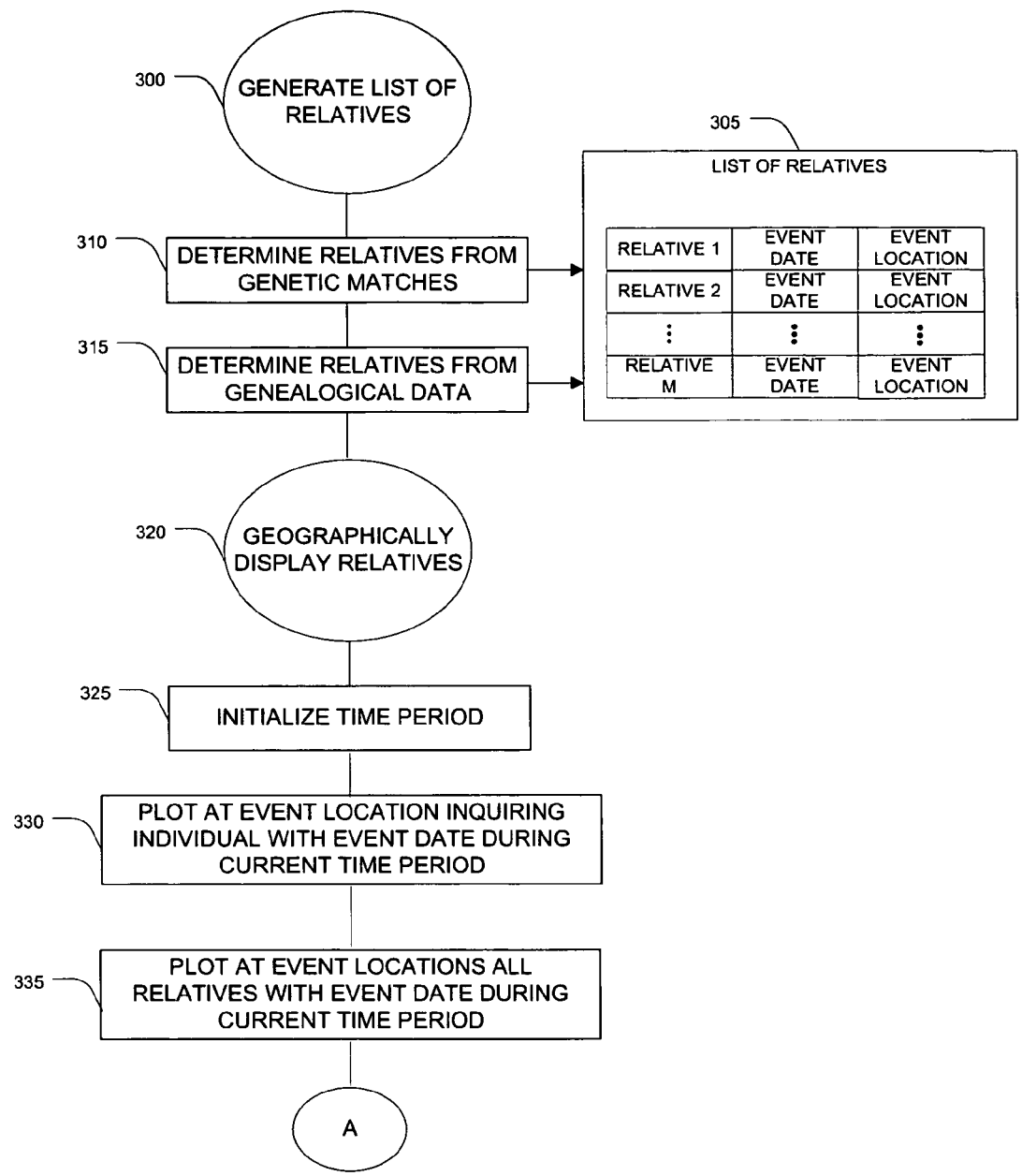
Figure 2C:
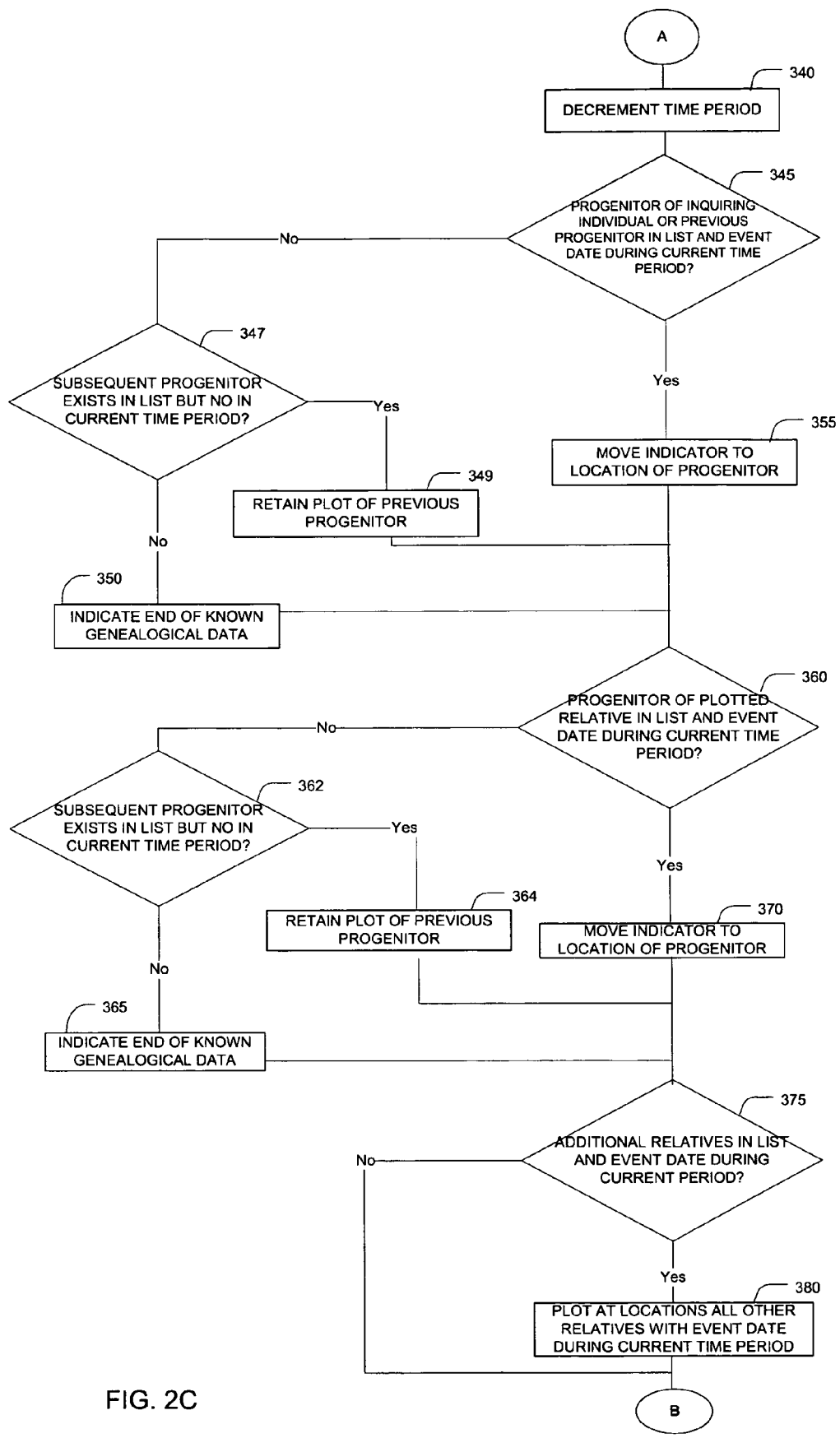
Figure 2D:
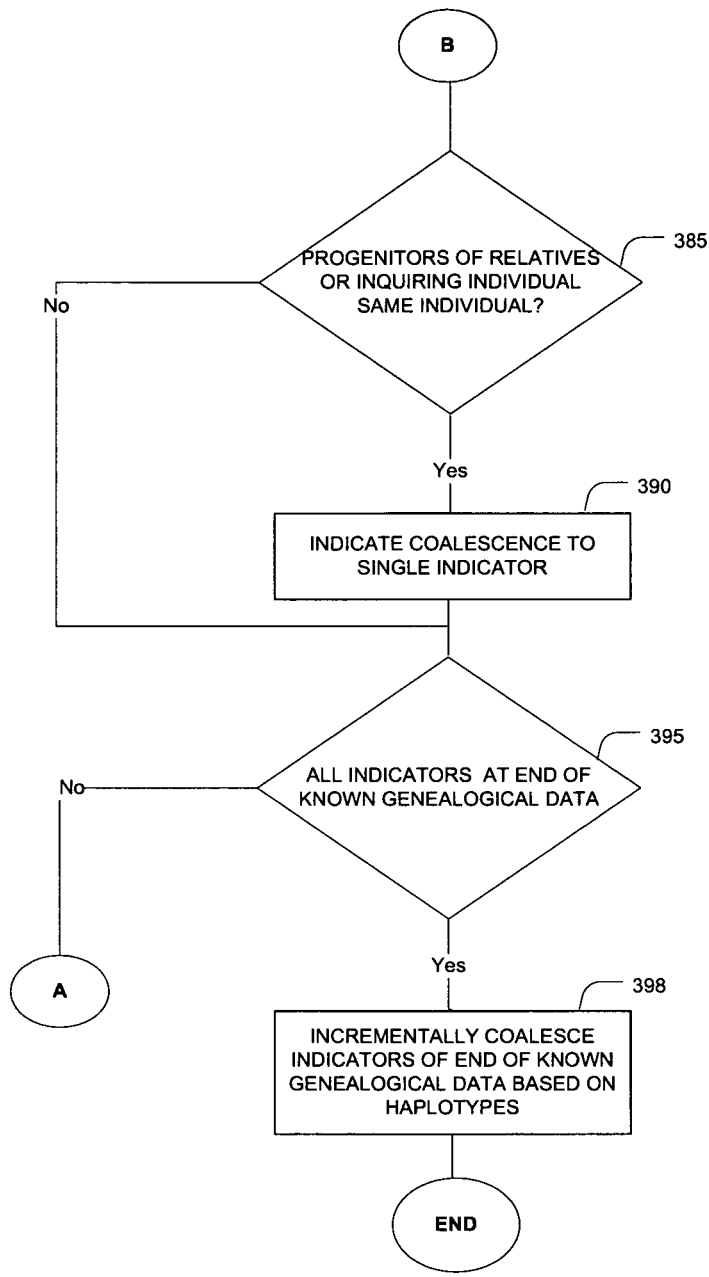
Figure 3A:
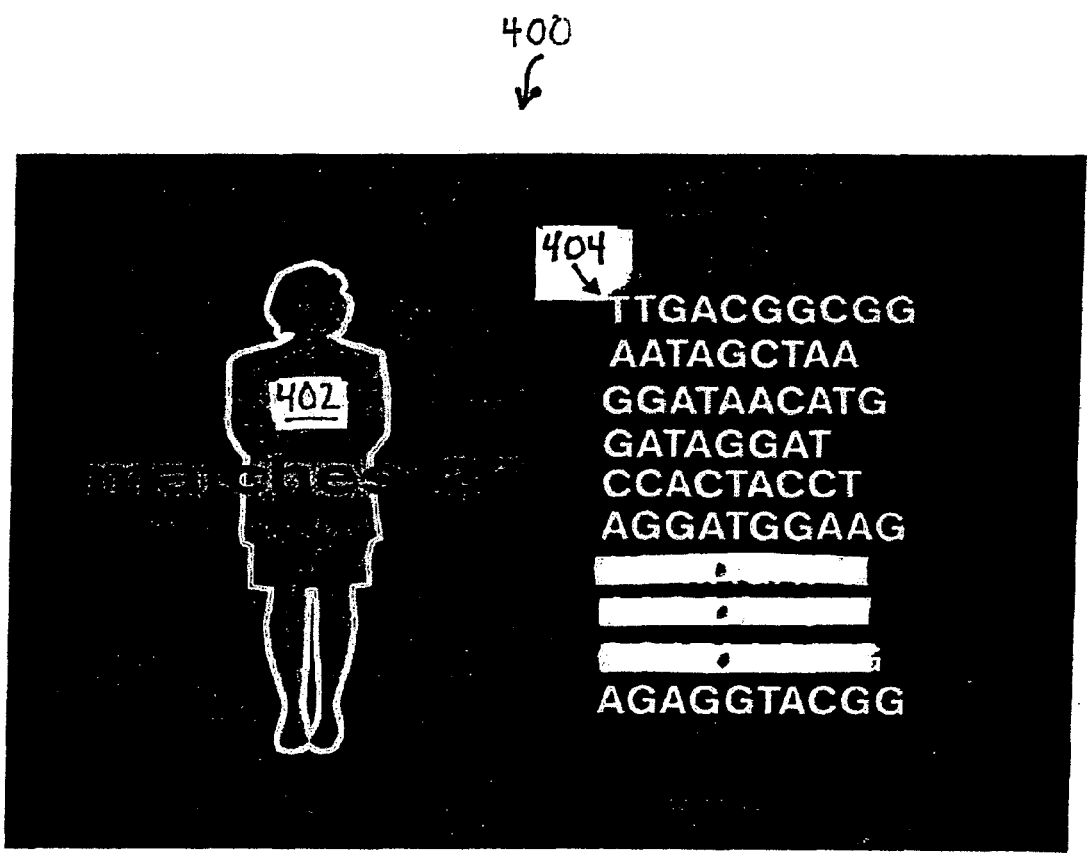
FIG. 3A includes (SEQ ID NO:1 of the SEQUENCE LISTING) (ttgacggcgg), (SEQ ID NO:2) (aatagctaa), (SEQ ID NO:3) (ggataacatg), (SEQ ID NO:4) (gataggat), (SEQ ID NO:5) (ccactacct), (SEQ ID NO:6) (aggatggaag) and (SEQ ID NO: 7) (agaggtacgg).

With reference to the method of displaying relatives of an individual embodiments of the present invention, FIG. 3A illustrates a visual depiction of a display 400 including an indicator 402 of a user or inquiring individual whose relatives are being visually displayed as determined from database 25 (FIG. 1). By way of example and not limitation, when one or more genetic matches 240 (FIG. 2) are identified, a quantity of the genetic matches may also be displayed 250 (FIG. 2) with visual indicators 404 (SEQ ID NOS:1-7) corresponding to identification of one or more of the genetic matches to the inquiring individual. Once genetic matches are determined and genealogical relationships are known for the inquiring individual and the genetic matches, a group of "relatives" of the inquiring individual may be formed and displayed.

Once the genetic matches are identified and alternatively displayed 250, the method generates 300 a list of relatives 305 (FIG. 2B). The list of relatives 305 is generated from the genetic data 30 (FIG. 1) and the genealogical data 40 (FIG. 1) located within database 25. Relatives are determined 310 from the genetic matches and added to the list of relatives 305. Additional relatives are also determined 315 from genealogical data and added to the list of relatives 305. The identified relatives further includes related information such as event dates (e.g., date of birth, date of christening/baptism, date of marriage, date of divorce, date of death, etc.) and the corresponding event location for the corresponding event. Genealogical records are not always exhaustive or complete with records identifying event date for the most desired life event. Some genealogical data includes locations associated with date of birth, date of death, date christening or baptism, dates of marriage, as well as other dates that indicate their existence at a particular geographic location. The presence of multiple time events in genealogical data for a specific individual may be prioritized such as date of birth, then date of christening/baptism, then date of marriage, then date of divorce, then date of death. Furthermore, acceptance of a lesser preferred life event in lieu of other life event data may also be utilized.

The process 320 of graphically displaying relatives of the inquiring individual may be presented across a domain of time. Using a time domain to display segments of time or time periods, a geographical display of the relatives may represent each relative during a period that includes the event date. By way of example and not limitation, FIGS. 3B-3G represent successive time periods over which the displaying process occurs. A displaying time period is initialized 325 and displayed as illustrated with respect to FIG. 3B. An indicator 402 of the inquiring individual is plotted 330 at the corresponding event location when their event date falls within the current time period being displayed on the geographical representation of FIG. 3B. Indicators 410, 412 of relatives from the relative list whose event dates fall within the current time period are plotted 335 at the respective event locations when the event dates fall within the current time period being displayed.

Figure 3C:
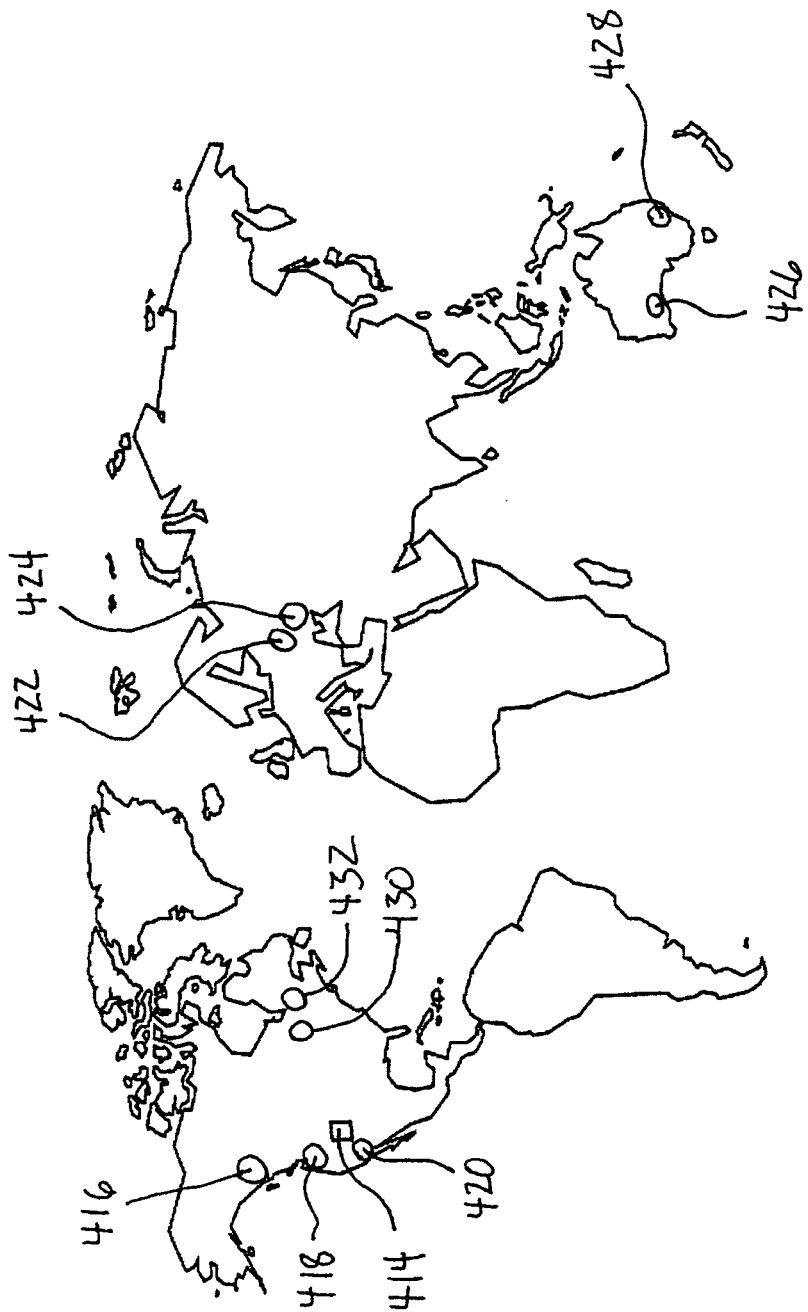
Figure 39:
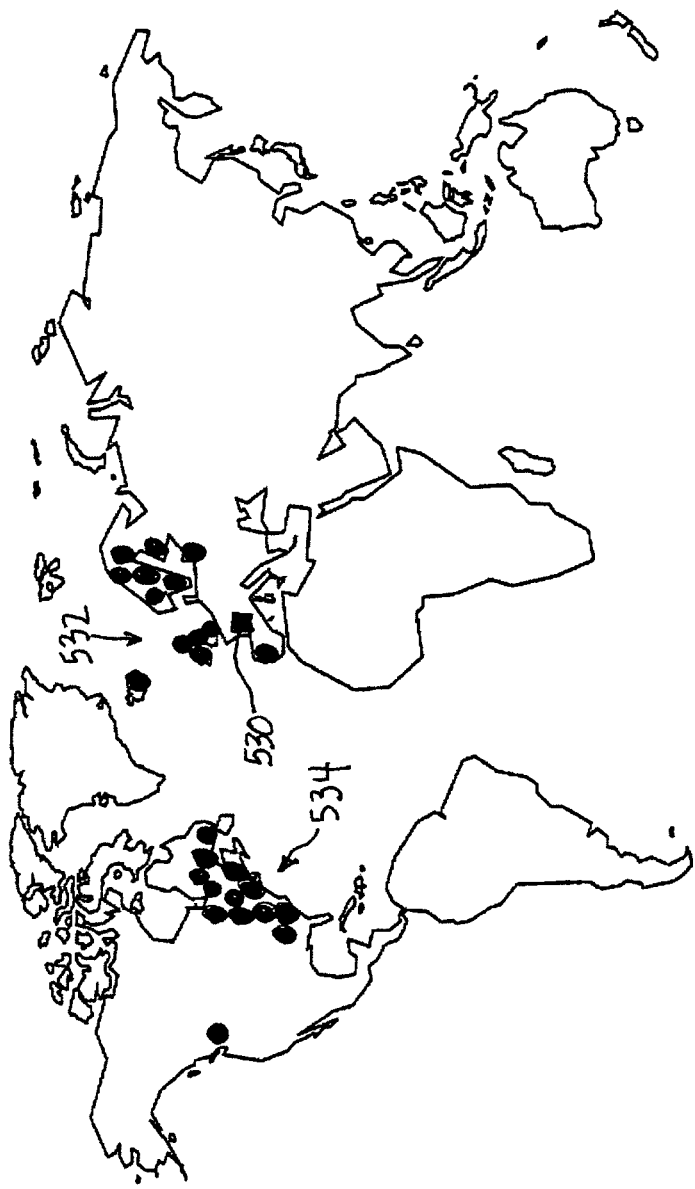

Once the display frame for a current time period is completed, the time period is decremented 340 as illustrated with reference to FIG. 3C. The display process determines 345 if progenitors of the inquiring individual or their previous progenitors exist within the list of relatives 305. If the display process determines 347 that progenitors exist but their event date is not within the current time period, the display process retains 349 the plot of the indicator 414 of the previous progenitor. If the display process determines 347 that no progenitors exist within the list of relative 305, then the display process indicates 350 an end of the genealogical data by differently displaying the indicator of the last known progenitor. If the display process determines 345 that a previous progenitor for the inquiring individual or a previous progenitor with an event date within the current time period is located within the list of relatives 305, a plot of the corresponding location is moved 355 to the corresponding event location of progenitor.

A similar process occurs to determine 360 if progenitors of the originally genetically related relatives exist within the list of relatives 305. If the display process determines 362 that progenitors exist but their event date is not within the current time period, the display process retains 364 the plot of the indicator 424, 426 of the previous progenitor. If the display process determines 362 that no progenitors exist within the list of relatives 305, then the display process indicates 365 an end of the genealogical data by differently displaying the indicator of the last known progenitor. If the display process determines 360 that a previous progenitor with an event date within the current time period is located within the list of relatives 305, a plot of the corresponding location is moved 370 to the corresponding event location of progenitor.

The display process determines 375 if additional relatives remain in the list of relatives 305 that have not yet been plotted as their corresponding event date has not arrived. Indicators 416-422, 428-432 of relatives from the relative list whose event dates fall within the current time period are plotted 380 at the respective event locations when the event dates fall within the current time period being displayed.

The display process also determines 385 if the relatives in the list of relatives converge to a common entity. If convergence to common entity is determined, then the display process indicates 390 convergence of multiple indicators of progenitors to a single indicator indicative of a common ancestor. The display process also determines 395 that all relatives from the list of relatives 305 have been displayed and no additional genealogical data is available for further plotting. If unplotted data remains in the list of relatives 305, then the display process returns to step 340 and the time period is further decremented and the process continues. If the display process determines 395 that all of the relatives in the relative list have been displayed and no additional genealogical data is available for further plotting, then all indicators should be differently indicating, resulting from steps 350, 365, an end of known genealogical data. Further incremental coalescence or converging 398 of data may occur based upon an understanding of various geographic locations of specific haplotypes or based upon the last recorded genealogical record associated with the converging lineages. The final common connection is based on geographic frequency estimates reported in primary scientific literature for a haplogroup defined by biallelic markers or unique event polymorphisms (UEPs).

FIGS. 3D-3G illustrate various subsequent renderings from the display process described with reference to FIG. 2. In FIG. 3D, the display process continues to determine 345, 360, 375 if progenitors of previously displayed indicators of relatives are present in the list of relatives 305. Indicators 440-456 and additional indicators depicted for clarity as indicator clusters 458, 460 are displayed according to the previously described process. FIG. 3D also illustrates a coalescence or convergence 462 of common ancestry into a common indicator 464 as described with respect to step 390 of FIG. 2D.

In FIG. 3E, the display process continues to determine 345, 360, 375 if progenitors of previously displayed indicators of relatives are present in the list of relatives 305. An indicator 470 illustrates the migration of a progenitor of the inquiring individual 402. Indicators 472-486 and additional indicators depicted for clarity as indicator clusters 488-492 are displayed according to the previously described process.

In FIG. 3F, the display process continues to determine 345, 360, 375 if progenitors of previously displayed indicators of relatives are present in the list of relatives 305. Indicators 500-512 and additional indicators depicted for clarity as indicator clusters 514, 516 are displayed according to the previously described process. FIG. 3E also illustrates by differently indicating 365 the ending of known genealogical data for a specific genetically related relative as illustrated by indicators 518, 520.

In FIG. 3G, several intermediate time periods are skipped for clarity sake. The display process continued to determine 345, 360, 375 progenitors until all known relatives in the list of relatives have been indicated. Indicator 530 differently indicates an end of known progenitors for the inquiring individual 402. Additionally, all other indictors depicted for clarity as indicator clusters 532, 534 also differently indicate an end of known progenitors of the genetic relatives of the inquiring individual.

Figure 4A:
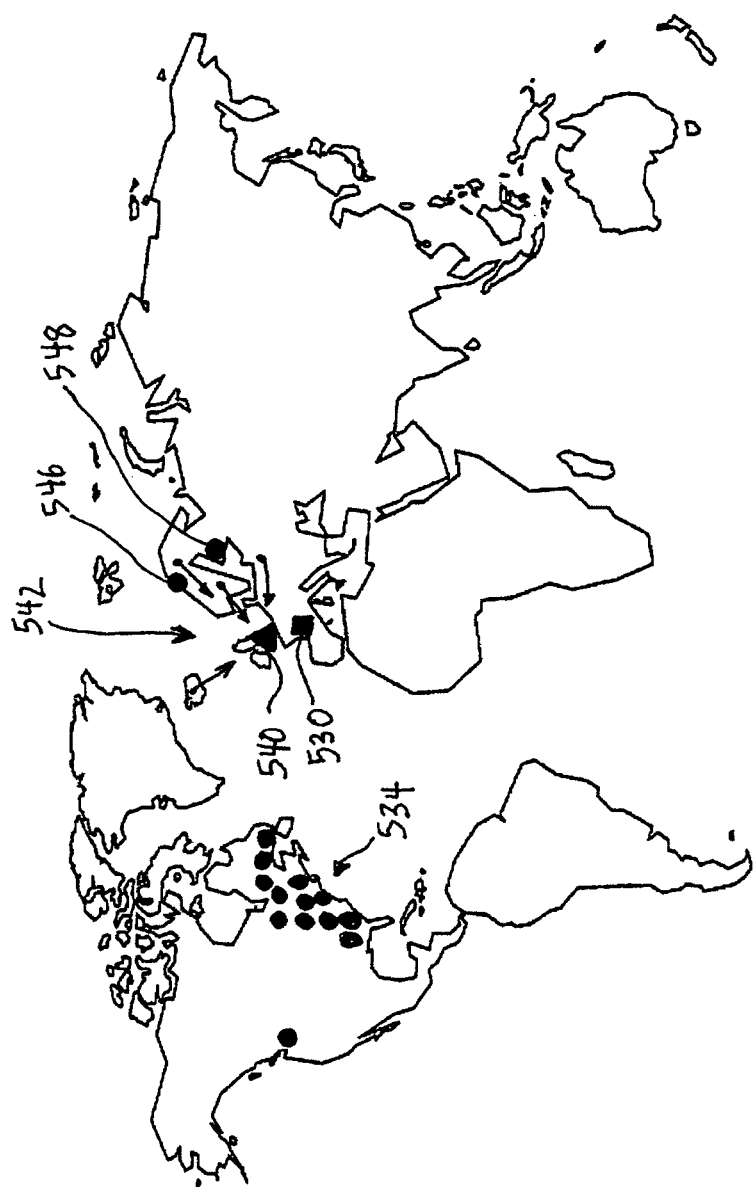
Figure 4C:

In FIGS. 4A-4C, the display process may incrementally coalesce indicators based upon haplotypes and the respective geographical location of the earliest genealogical event determined from coalescing lineages. FIG. 4A illustrates a first coalescence of various ones 542 of the indicators which include common genetic characteristics that denote a strong likelihood of common ancestry. The various genetically related indicators coalesce into a common indicator 540.

FIG. 4B illustrates a subsequent coalescence of various ones 552 of the indicators 546, 548 (FIG. 4A), which include common genetic characteristics that denote a strong likelihood of common ancestry. It should be noted that common indicators also coalesce when relatedness is found with other individual indicators or other common indicators. In FIG. 4B, the various genetically related indicators coalesce into a common indicator 550.

Any number of gradations of coalescence may be defined, however, FIG. 4C illustrates a final coalescence of various common or individual indicators which include common genetic characteristics that denote a strong likelihood of common ancestry. In FIG. 4C, the various genetically related indicators coalesce into a common indicator 560.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A method of displaying indicators of related individuals, the method comprising:

providing genealogical data of an inquiring individual corresponding to at least one known progenitor;

associating a genetic input of the inquiring individual with the genealogical data of the inquiring individual, wherein the genetic input includes data comprising at least one of a Y-chromosome (Y-cs), mitochondrial DNA (mtDNA), and autosomal (A) gene or marker contained on a non-sex chromosome;

identifying, by a processor and from a genetic database stored on a computer-readable medium in response to the genetic input of the inquiring individual, one or more individuals having a shared ancestry with the inquiring individual, wherein the genetic database includes data comprising at least one of a Y-cs, mtDNA, and A gene or marker contained on a non-sex chromosome, and wherein at least one of the one or more individuals having a shared ancestry with the inquiring individual was unknown to the inquiring individual at the time of the identification; and displaying indicators of the inquiring individual and each of the one or more individuals; having a shared ancestry with the inquiring individual, wherein the data included in the genetic input includes at least one of a genetic marker and a chromosomal fragment identified from a biological sample including genetic material obtained from the inquiring individual.

2. The method of claim 1, comprising displaying indicators of genealogically related individuals having a shared ancestry with the inquiring individual from a genealogical database corresponding to the inquiring individual and each of the genealogically related individuals, so as to indicate the existence of the inquiring individual and genealogically related individuals at a particular geographic location.

3. The method of claim 2, wherein displaying indicators of genealogically related individuals having a shared ancestry with the inquiring individual comprises sequentially displaying the indicators of the genealogically related individuals according to time increments corresponding to life events of each of the genealogically related individuals.

4. The method of claim 3, wherein the life event is selected from the group consisting of birth, a religious event, a legal event, and death.

5. The method of claim 3, wherein displaying indicators of genealogically related individuals having a shared ancestry with the inquiring individual according to time increments comprises replacing the indicator of one of the genealogically related individuals with the indicator of a different genealogically related individual when the time increment temporally precedes the life event.

6. The method of claim 3, wherein displaying indicators of genealogically related individuals having a shared ancestry with the inquiring individual according to time increments comprises differently displaying an indicator when no predecessor of the indicated individual exists in the genealogical database.

7. The method of claim 3, wherein the time increment corresponds to a quantity of years.

8. The method of claim 7, wherein the time increment corresponds to the quantity of years of an approximate generation.

9. The method of claim 2, further comprising combining one or more of the indicators of individuals having a shared ancestry with the inquiring individual at the particular geographical location when no predecessors of the indicated individuals exist in the genealogical database and when the indicators to be combined include genetic similarities common to the particular geographical location.

10. The method of claim 1, wherein the data included in the genetic database consists of Y-chromosome genes and/or markers.

11. The method of claim 1, wherein the data included in the genetic database consists of mitochondrial genes and/or markers.

12. The method of claim 1, wherein the data included in the genetic database consists of autosomal genes and/or markers.

13. The method of claim 1, wherein identifying one or more individuals comprises identifying at least one of the one or more individuals from the genetic database that is within a first threshold of differences from the genetic input of the inquiring individual.

14. The method of claim 13, wherein the first threshold of differences is reduced when the quantity of the one or more individuals exceeds a second threshold.

15. A method of displaying indicators of related individuals, the method comprising:
obtaining a biological sample including genetic material obtained from an inquiring individual;
determining a genetic input of the inquiring individual, wherein the data included in the genetic input includes at least one of a Y-chromosome (Y-cs), mitochondrial DNA (mtDNA), and autosomal (A) gene or marker contained on a non-sex chromosome identified from the biological sample including genetic material obtained from the inquiring individual;
providing genealogical data, of the inquiring individual, corresponding to at least one known progenitor;
associating the genetic input of the inquiring individual with the genealogical data of the inquiring individual;
identifying, by a processor and from a genetic database stored on a computer-readable medium in response to the genetic input of the inquiring individual, one or more individuals having a shared ancestry with the inquiring individual, wherein the genetic database includes data comprising at least one of a Y-cs, mtDNA, and A gene or marker contained on a non-sex chromosome, and wherein at least one of the one or more individuals having a shared ancestry with the inquiring individual was unknown to the inquiring individual at the time of the identification; and
displaying indicators of the inquiring individual and each of the one or more individuals having a shared ancestry with the inquiring individual.

16. The method of claim 15, comprising displaying indicators of genealogically related individuals having a shared ancestry with the inquiring individual from a genealogical database corresponding to the inquiring individual and each of the genealogically related individuals, so as to indicate the existence of the inquiring individual and genealogically related individuals at a particular geographic location.

17. The method of claim 16, wherein displaying indicators of genealogically related individuals having a shared ancestry with the inquiring individual comprises sequentially displaying the indicators of the genealogically related individuals according to time increments corresponding to life events of the genealogically related individuals.

18. The method of claim 17, wherein the life event is selected from the group consisting of birth, a religious event, a legal event, and death.

19. The method of claim 17, wherein displaying indicators of genealogically related individuals having a shared ancestry with the inquiring individual according to time increments comprises replacing the indicator of one of the genealogically related individuals with the indicator of a different genealogically related individual when the time increment temporally precedes the life event.

20. The method of claim 17, wherein displaying indicators of genealogically related individuals having a shared ancestry with the inquiring individual according to time increments comprises differently displaying an indicator when no predecessor of the indicated individual exists in the genealogical database.

21. The method of claim 17, wherein the time increment corresponds to a quantity of years.

22. The method of claim 21, wherein the time increment corresponds to the quantity of years of an approximate generation.

23. The method of claim 17, further comprising combining one or more of the indicators of individuals having a shared ancestry with the inquiring individual at the particular geographical location when no predecessors of the indicated individuals exist in the genealogical database and when the indicators to be combined include genetic similarities common to the particular geographical location.

24. The method of claim 1, wherein the data included in the genetic database consists of Y-chromosome genes and/or markers.

25. The method of claim 1, wherein the data included in the genetic database consists of mitochondrial genes and/or markers.

26. The method of claim 1, wherein the data included in the genetic database consists of autosomal genes and/or markers.

* * * * *